United States Patent [19]

Collins et al.

[11] Patent Number: 4,856,517
[45] Date of Patent: Aug. 15, 1989

[54] UMBILICAL CORD CLAMP APPARATUS

[76] Inventors: Jason H. Collins, 1344 Covington Highway, Slidell, La. 70460; Robert G. Woodhead, 18 Krebbs Rd., Plainsboro, N.J. 08536

[21] Appl. No.: 66,602

[22] Filed: Jun. 26, 1987

Related U.S. Application Data

[63] Continuation-in-part of Ser. No. 909,883, Sep. 22, 1986, Pat. No. 4,781,188.

[51] Int. Cl.[4] ............................................. A61B 17/12
[52] U.S. Cl. ................................... 128/346; 128/305
[58] Field of Search ................. 128/305, 325, 346, 314

[56] References Cited

U.S. PATENT DOCUMENTS

| | | | |
|---|---|---|---|
| 2,524,337 | 10/1950 | Whittaker | 128/305 |
| 2,556,036 | 6/1951 | Jensen | 128/305 |
| 3,705,586 | 12/1972 | Sarracino | 128/346 |
| 4,428,374 | 1/1984 | Auburn | 128/346 X |
| 4,572,181 | 2/1986 | Mattler | 128/346 X |
| 4,602,629 | 7/1986 | Schmirman | 128/346 X |
| 4,648,401 | 3/1987 | Mattson | 128/346 X |
| 4,716,886 | 1/1988 | Schulman et al. | 128/346 X |

Primary Examiner—Dalton L. Truluck
Assistant Examiner—Denise Whelton
Attorney, Agent, or Firm—Pravel, Gambrell, Hewitt, Kimball & Krieger

[57] ABSTRACT

An improved umbilical cord clipper apparatus constructed of non-metallic material having a base portion and a top portion movable between open and closed positions in relation to one another via a loop hinge on their common end portion. The apparatus further comprises first and second recesses in the base and top portion for positioning of an umbilical clamp of the type which would incorporate a pair of elongated arms and a loop portion as disclosed in U.S. Pat. No. 3,854,482. The pair of clamps are positioned with a space therebetween, so that a blade member housed in the floor of the base portion, flies intermediate the two clamp members positioned therein. Further, there is provided a pair of flexing members within the hinged loop so that the clamp when in position within the base of the apparatus are engaged the bias of the members.

9 Claims, 4 Drawing Sheets

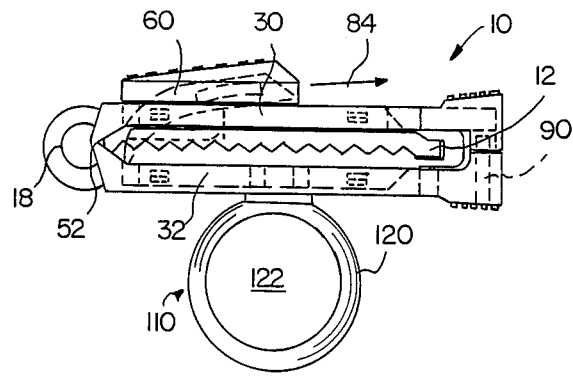
FIG. 19
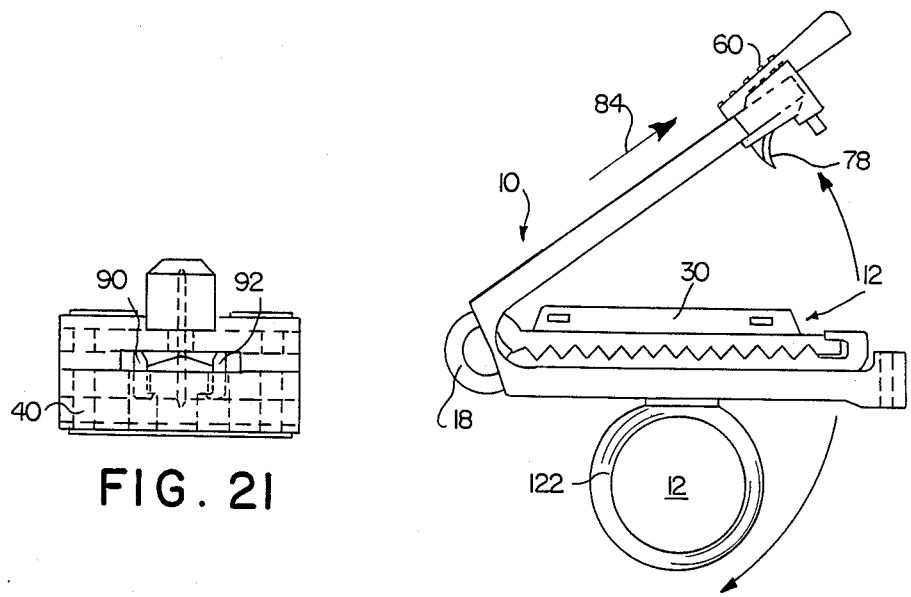
FIG. 21
FIG. 20
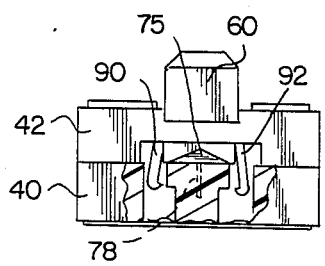
FIG. 22

UMBILICAL CORD CLAMP APPARATUS

This is a Continuation-in-Part application on U.S. application Ser. No. 06/909,883, entitled "Umbilical Cord Clamp Apparatus", filed on Sept. 22, 1986, by the same inventor, and is presently pending now U.S. Pat. No. 4,781,188.

BACKGROUND OF THE INVENTION:

1. Field of the Invention:

The apparatus of the present invention relates to clamps. More particularly, the present invention relates to an apparatus for housing a pair of umbilical clamps, the housing having a movable blade between the clamps, so that the clamps may clamp portions of the umbilical cord and simultaneously the blade will sever the end of the cord intermediate the clamps in a single step.

2. General Background:

In the science of the delivery of babies, following the removal of the baby from the mother, it is necessary that the umbilical cord, through which the baby is receiving its blood supply and nutrients from the mother, is severed, and the loss of blood from the cord be interrupted. Therefore, in the present state of the art, this procedure is basically accomplished in three steps. First, the cord is clamped with two separate clamps, with a space between the clamps, and the third step is that the cord is then severed. Therefore, no blood is lost either from the baby nor from the mother's placenta, and the baby's cord is then permanently tied off, and the placenta is then removed from the mother to prevent any further loss of blood.

Practice has it that this obstetric procedure during the delivery of the baby is somewhat time consuming, and may be simplified. It would therefore be beneficial to the servicing physician, that following the delivery of the baby, that there be an instrument which would enable the physician to quickly clamp and cut the cord through perhaps a single step, which would eliminate any of the unnecessary steps which are now undertaken.

In addressing the question of this type, several patents have been issued, the most pertinent being as follows:

U.S. Pat. No. 3,315,679 issued to Sarracino, entitled "Umbilical Cord Clamp", simply teaches the use of a single clamp which provides jaw faces on which faces are formed complementary, serrated, angulated surfaces. A spring or the like is provided for resiliently biasing the surfaces toward one another in engagement with the umbilical stump.

U.S. Pat. No. 3,040,749 issued to Paten, entitled "Umbilical Cord Clamp", likewise provides an expendable and disposable umbilical cord clamp apparatus which has generally parallel clamping members when the clamp is closed, and has a permanently lock that can not be released following the closing of the clamp.

U.S. Pat. No. 2,307,377 issued to Riccardi, entitled "Umbilical Clip", also teaches the use of a clip which can be placed upon a pair of forceps or the like, and upon engaging the clamping member in locking the clamp in place, the forceps are removed and the clamp remains on the umbilical cord.

U.S. Pat. No. 2,626,608 issued to Garland, entitled "Clamp For Umbilical Cords Or The Like", likewise teaches the use of a clamp which can be place upon a pair of pliers and once engaged, the plyer member bend into a position that remains in the clamped position during use.

U.S. Pat. No. 3,705,586 issued to Sarracino, entitled "Umbilical Cord Clamp", addresses the use of an umbilical clamp having serrated edges that because of the edges and the inner locking of the clamp will remain in place over a period of days.

U.S. Pat. No. 1,710,766 issued to Dilworth, entitled "Umbilical Cord", relates to an umbilical clamp which is slipped onto the umbilical cord and is clamp into place while simultaneously severing the umbilical cord at the joint of clamping.

U.S. Pat. No. 1,843,652 issued to Taylor, entitled "Umbilical Cord Clamp", in which two pieces of sheet metal or pivoted on one another being held flatly in place by means of a pivotal pin. Each of the pieces of metal having a cut out which constitutes jaws of the clamp and effects closure of the cut joint opening which exists when the cut outs overlay one another.

U.S. Pat. No. 2,498,372 issued to Kortlucke, Jr., et al, entitled Clamping Device", also teaches the use of a clamp of the type that has serrated edges and closes upon the item to be clamped with it locking in place around the second end portion.

U.S. Pat. No. 2,434,831 issued to Brandenburg, entitled "Umbilical Clip And Holder For Same", teaches the use of an umbilical clip which is placed in position on a pair of forceps; after clamping takes places the forceps are removed therefrom with the clamp being maintained in the closed position.

U.S. Pat. No. 2,524,377 to Whittaker, entitled "Umbilical Clamp And Cutter", to a clamp for simultaneously clamping the umbilical at two spaced points in cutting the cord between the points.

U.S. Pat. No. 3,854,482 to Laugherty, et al, entitled "Umbilical Cord Clamp", the use of an umbilical cord clamp made of non-metallic material with a pair of elongated arms joined at a loop and a locking means on the second hand for clamp in the closed position following clamping cord.

SUMMARY OF THE PRESENT INVENTION:

The apparatus of the present invention is an improvement over the umbilical cord clamp apparatus as disclosed and claimed in U.S. patent application, Ser. No. 909,883, filed by the same inventor. What is provided is an improved umbilical cord clamp apparatus constructed of non-metallic material having a base portion and a top portion movable between open and closed positions in relation to one another via a hinge on their common end portion. The apparatus further comprises first and second recesses in the base and top portion for positioning of an umbilical clamp of the type which would incorporate a pair of elongated arms and a loop portion as disclosed, as disclosed in U.S. Pat. No. 3,854,482, with the clamps automatically locked closed when placed in the closed position. The pair of clamps are positioned with a space there between, so that a blade member movably housed in the upper portion of the holder, a traveler intermediate the two clamp members positioned there. Further, there is provided a locking member on the front portion of the holder to lock the holder in the closed position while the clamps have engaged the umbilical cord. In use, the umbilical cord is positioned within the space between the upper and lower portions of the apparatus, the apparatus is moved to the closed position and locked closed, thus locking the umbilical clamps closed. Simultaneously, the blade member is moved forward in its track by the thumb and severs the umbilical cord. As the blade travels further, the blade engages the button which makes contact with the locking mechanism of the apparatus and allows the apparatus to return to the open position, with the clamps being maintained locked in the closed position. There is further included a holder on the lower base of the apparatus wherein the index finger is inserted therethrough so that when the apparatus is returned to the open position, the apparatus is retrieved from the clamps and the clamps are maintained on the severed umbilical cord.

BRIEF DESCRIPTION OF THE DRAWINGS:

FIG. 19 is a side partial cut away view of the preferred embodiment of the apparatus of the present invention in the closed position;

FIG. 20 is a side view of the preferred embodiment of the apparatus of the present invention in the open position following the cutting action; and FIGS. 20 and 21 are front partial cut away views of the preferred embodiment of the apparatus of the present invention illustrating the motion of the cutting assembly end unlocking the apparatus as seen in FIG. 19 so that it may move to the open position as seen in FIG. 20.

DETAILED DESCRIPTION OF THE PREFERRED EMBODIMENT:

FIGS. 1–21 illustrate by the numeral 10 the preferred embodiment of the apparatus of the present invention. However, prior to a discussion of the apparatus as viewed in the FIGURES, reference shall be made to FIGS. 2–5 which represent views of a modified clamp apparatus which is utilized in conjunction with the apparatus 10 of the present invention.

Figure 3:
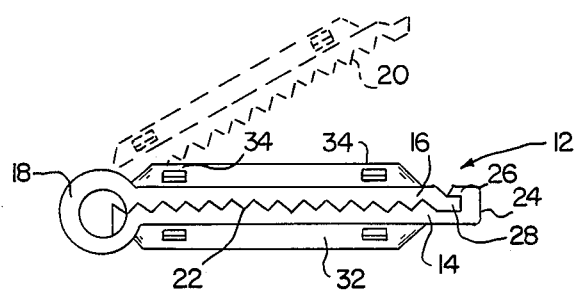
Figure 4:
Figure 5:
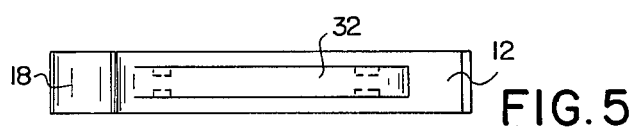

As seen in FIGS. 2–5, there is illustrated a clamp apparatus 12 constructed in such a manner as to have a base portion 14, an upper portion 16, the base portion 14 and upper portion 16 hingedly attached through rear ring hinge 18, and being integrally attached thereto so that clamp 12 is normally in the open position as seen in phantom view in FIG. 3. Clamp 12 would have a plurality of teeth members 20 on the upper and lower faces respectively of the upper portion 16 and base portion 14, so that in the closed position as seen in FIG. 3, teeth members 20 mesh to form a continuous locking arrangement 22, as seen in FIG. 3. In order to maintain the clamp apparatus in the closed position there is provided a locking means 24 which includes, on its base portion 14, an overlapping tooth member 26 which engages a shoulder portion 28 in the upper portion 16, so that mechanism 12 is locked in the closed position. Structurally, clamp 12 provides an upper rib member 30 and a lower rib member 32, the upper rib member 30 and lower rib member 32 insertable into apparatus 10 as will be discussed further, with the upper and lower rib members including a pair of locking recesses 34 in the side walls of each upper and lower rib members 30 and 32, recesses 34 accommodating tabs on the body of apparatus 10 to maintain clamp 12 in position as will be seen further. For purposes of use of course, clamp 12 is a typical umbilical clamp, although modified for particular use in conjunction with apparatus 10, which is utilized in clamping off of the umbilical cord 11 as seen in FIG. 1, after the baby has been removed from the womb, and the cord must be severed.

In the present state of the art, as was discussed earlier, a pair of clamps 12 are locked into position around umbilical cord 11, and a surgical knife or the like severs umbilical cord 11 intermediate the pair of clamps 12, so that bleeding does not occur either from the mother's side or the baby's side of the umbilical cord. Apparatus 10 is constructed so as to accommodate a pair of clamps 12 and a cutting assembly situated intermediate the clamps 12 so that the clamps 12 can be locked into position and the umbilical cord severed in a single motion by the doctor, and upon opening, apparatus 10 can be removed from the cord with the clamps 12 in locked position, thus eliminating the cumbersome and time consuming steps of individually clamping each clamp and severing the cord therebetween.

Figure 1:
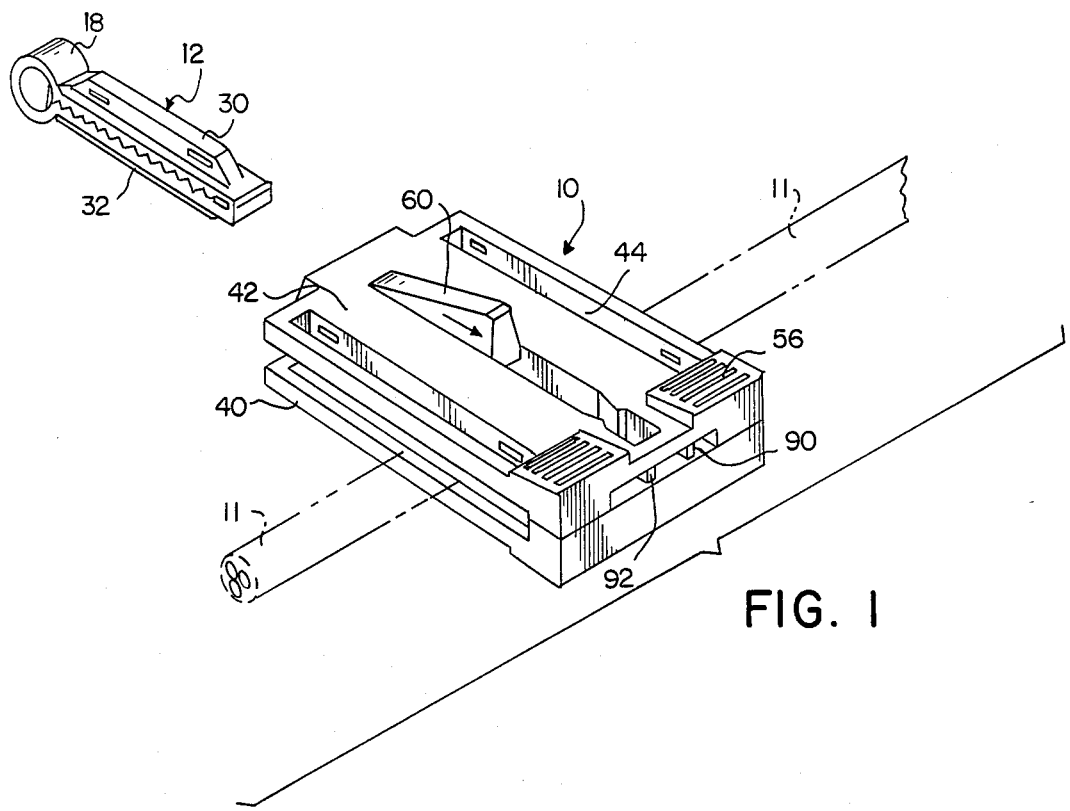
FIG. 1 is an overall perspective view of the preferred embodiment of the apparatus of the present invention.
Figure 2:
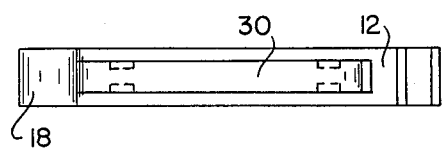
FIGS. 2–5 are views of the modified umbilical clamp insertable into the apparatus of the present invention.

Turning now to the apparatus 10 as was discussed in the previous paragraph, in FIG. 1 there is illustrated apparatus 10 in the locked position around umbilical cord 11, with apparatus 10 housing a pair of clamps 12 as is illustrated having been removed for illustrative purposes, but in use, as seen in FIGS. 19 and 20, clamps 12 would be positioned within apparatus 10 at this point.

As seen in the FIGURES, apparatus 10 includes a generally rectangular base portion 40, an upper hingedly attached upper portion 42, which likewise is rectangular in shape, and for the most part so that in the closed position base portion 40 and upper portion 42 match to form the singular closed apparatus as seen in FIG. 1.

Further, base portion 40 includes a pair of channels 44 and 46 running substantially along its length, a pair of channels therefore accommodating the lower rib portion 32 of a clamp 12 to lock it into position with tabs 48 as illustrated in the FIGURES locking inter-recesses 34 in the upper and lower rib portions 30 and 32 respectively in the apparatus of clamp 12, so that the upper and lower portions 14 and 16 are locked into position as seen in the FIG. 19. Likewise, upper portion 42 also has a pair of channels 48 which coincide with the lower channels 48 and base portion 40, so that the upper rib 30 of upper portion 16 of clamp 12 are likewise locked into position via tabs 48 for the same reason as explained earlier.

Figure 8:
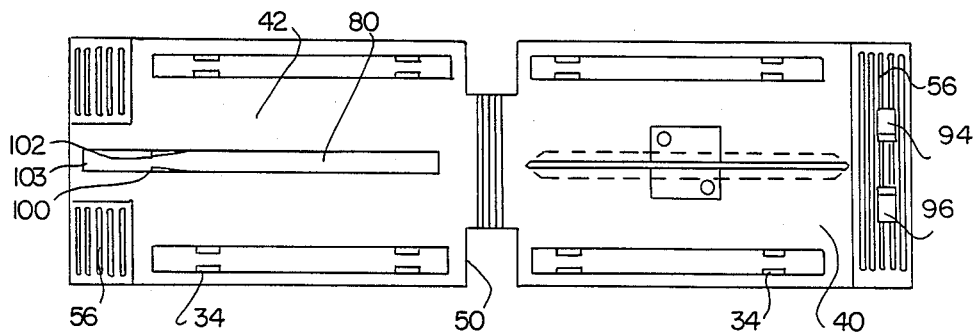

As seen in side view, base portion 40 an upper portion 42 are connectedly engaged in their portions 50 via a hinge member 52, which includes an integral clasping hinge 54 standing between base portion 40 and upper portion 42, for accommodating free movement of base portion 40 and upper portion 42 between open and closed positions as seen in FIGS. 19 and 20. As seen in the underside view in FIG. 8, the upper face of upper portion 42 and the lower face of lower portion 40 as seen in FIG. 8, include a means for engaging both a means 56 which comprises a series of ribbed members for gripping the upper and lower portions as the apparatus is manipulated in use.

Figure 13:
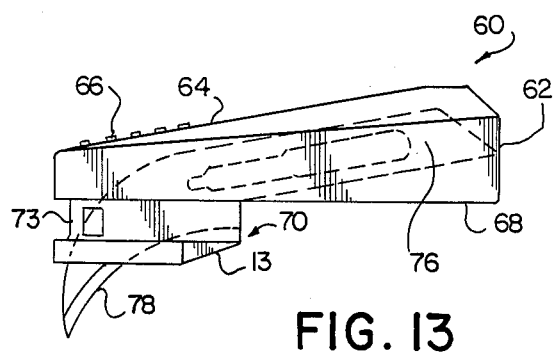

Following the positioning of a pair of clamp members 12, within apparatus 10 as seen more clearly in FIGS. 19 and 20, another most important feature of the apparatus 10 is the accommodations of the cutting assembly 60 as seen in full view in FIG. 13. As seen in the FIGS. 11-15 in cutting assembly 60 is illustrated independent of the apparatus 10. A discussion will be had thereafter of the mounting of cutting assembly 60 within apparatus 10 in its functioning thereof. However, turning now to cutting means 60 as viewed in the FIGURES, cutting means 60 would include an upper principal housing 62 having an upper face portion 64 and a gripping portion 66 with a placement of one's thumb or the like during the cutting action. Further, housing 62 has a lower face portion 68 with attached thereto a mounting assembly 70 which includes a narrowed neck portion 72 which would be slidably engaged in the base of apparatus 10 that will be discussed further. Further there is included a lower most shoulder portion 74 which maintains a cutting assembly 60 within a channel in the base portion of apparatus 10, during the cutting action. Cutting assembly 60 further includes a surgical blade member 76 which could be injection molded or the like into the body portion 62 of assembly 60, the sharpened cutting portion 78 extruding from the lower mounting portion 70, blade 78 slidably movable between front and rear positions along apparatus 10 as will be discussed further.

Turning now to the mounting of blade assembly 60 within apparatus 10, the upper portion 42 of apparatus 10 includes a centrally located channel 80, running upon its length, accommodating neck portion 72 therewithin, with the lower most blade portion 78 extruding from the underside of upper housing 42 as seen in FIGS. 19 and 20. In the closed position, blade portion 78 would extrude to a point below the upper face of base portion 40. Therefore, base portion 40 includes a narrow channel 82 for accommodating the blade 78 as it slides from the first rear position as seen in FIG. 19 to the forward position as seen in FIG. 20 in the direction of Arrow 84. Therefore, in the movement of the assembly 60 while the apparatus is in the closed position, blade 78 would come into contact with umbilical cord 11 clampedly engaged in the clamp members 12 as seen in FIG. 19, and would sever umbilical cord 11 during the movement from the rear position as seen in FIG. 19 to the forward position as seen in FIG. 20.

Figure 9:
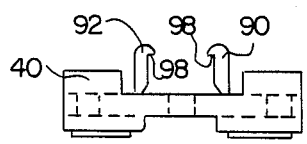
FIGS. 9 and 10 are front and rear views respectively of the preferred embodiment of the apparatus of the present invention.
Figure 10:
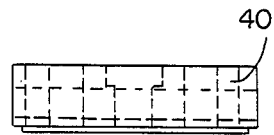
Figure 11:
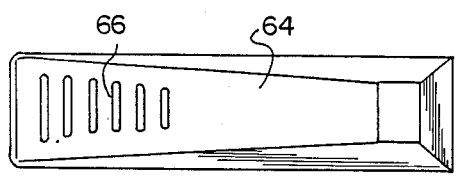
FIGS. 11–15 are views of the cutting assembly of the preferred embodiment of the apparatus of the present invention.
Figure 12:
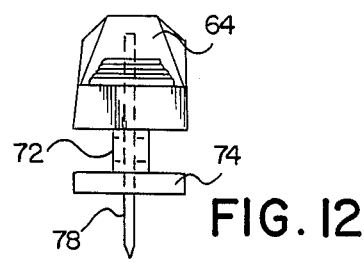

An additional feature of the present invention, is the ability of apparatus 10 to become locked into the closed position as seen in FIG. 19. As was discussed earlier, in the structure of clamp 12, clamp 12 included a locking means 24 on its forward end whereby clamp 12 would be locked into the closed position as seen in FIGS. 3 and 19. In addition, apparatus 10 would likewise be locked into position via a pair of locking members 90 and 92 as seen in FIG. 9. Locking members 90 and 92 are simply a pair of raised arm members fused into the base 40 of apparatus 10 and would engage a pair of slots 94 and 96 as seen in the upper portion 42 of the apparatus. Therefore, upon being placed in the closed position as seen in FIG. 19, tab members 90 and 92 would flexibly move through slots 94 and 96 respectively, as seen in FIG. 21, and would lock into position via teeth members 98 engaging the floor portion of base 40 as seen in FIG. 21.

Figure 14:
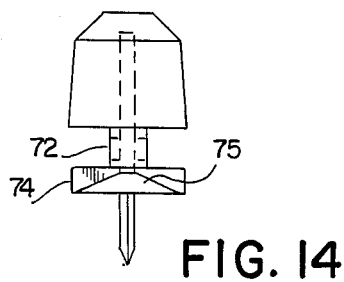
Figure 15:
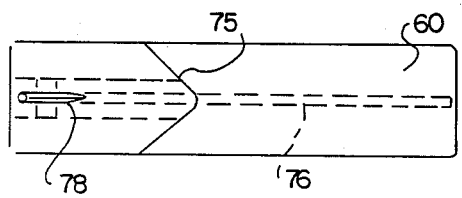

However, it should be noted that for purposes of use of the apparatus, following the cutting action of blade assembly 60 as was discussed previously, there is included a means for disengaging tab members 90 and 92 from the locked position to the unlocked position so that apparatus 10 may be moved to the open position as seen in FIG. 20 and retrieved maintaining clamp members 12 into the locked engagement around umbilical cord 11. This means is illustrated in the FIGURES, particularly FIG. 22. This means is illustrated in FIGS. 11-15, illustrating cutting assembly 60 and in FIG. 22 showing the movement of blade assembly in unlocking the apparatus. As seen in FIG. 14, the front lower base portion 74 cutting assembly is positioned along the underside of top portion 42 of the apparatus as the neck portion 72 is engaged within upper slot 80. It should be noted that base portion 74 has a front beveled face 75 which as seen in side view in FIG. 13 would move forward to engage the pair of tabs 90 and 92 and move them to the out position as seen in FIG. 22. This engagement would therefore move teeth members out of locking engagement with floor portion of base 40, and would allow apparatus 10 to move to the open position as seen in FIG. 20. Therefore, apparatus 10 could be thereby retrieved from clamps 12 that are maintained in the locked position.

In addition, following the cutting action of blade assembly 60 as seen in FIG. 20, it is preferred that cutting assembly 60 be maintained in the forward position since the cutting action of blade assembly 60 is completed. This is insured with a pair of tab members 100 and 102 situated in channel 80 and upper portion 42, which extrude out into the space of channel 80. As the assembly 60 is moved forward as the rear wall 73 which moves past tabs 100 and 102 into space 103 and therefore tabs 100 and 102 then engage rear wall 73 and prevent any further movement of blade 60 back into the first position as seen in FIG. 19.

Figure 6:
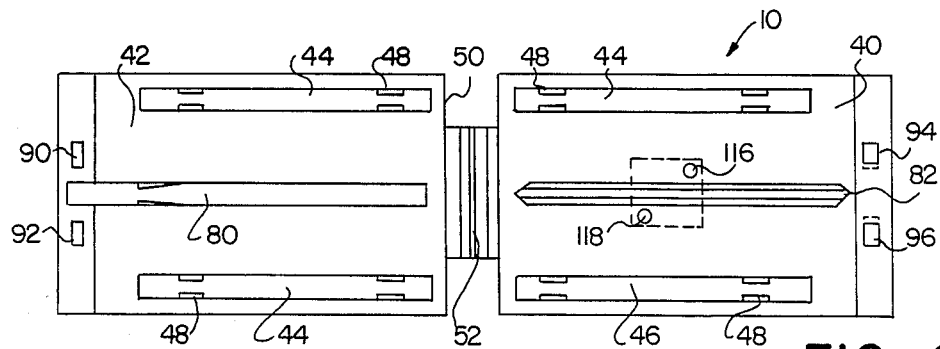
FIGS. 6–8 are top, side, and bottom views of the preferred embodiment of the apparatus of the present invention in the open position.
Figure 7:
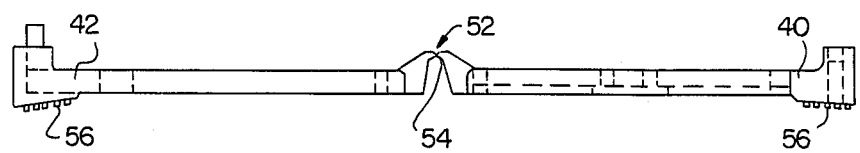
Figures 16, 17:
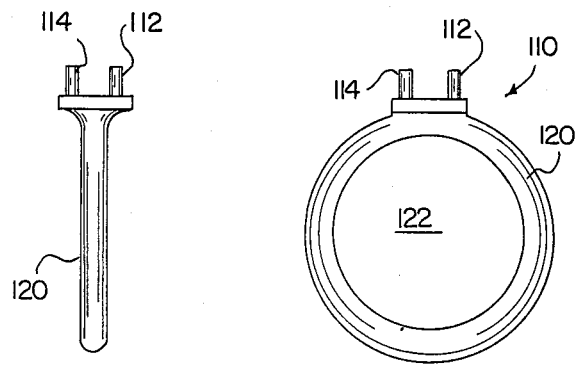
FIGS. 16–18 are side, front, and top views respectively of the holding assembly of the preferred embodiment of the apparatus of the present invention.
Figure 18:
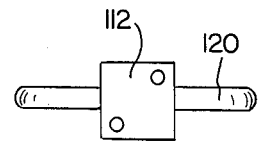

An additional aspect of the present invention is the presence of a holding means 110 as seen in FIGS. 16-18. Holding means 10 includes a base portion 112 which is mountable onto the underside of base portion 40 through a pair of tabs 112 and 114 insertable into ports 116 and 118 as seen in FIG. 6. Inserts 112 and 114 are melted or molded into position, maintaining holding means 110 into position on the underside of the apparatus as seen in FIG. 19. Holding means 110 further includes a ring member 120 having a central bore 112 wherein a finger is inserted therethrough, for holding apparatus 10 via the index finger through bore 122 and operating blade 60 with the thumb or the like.

In addition, after blade assembly 60 is moved to the forward position and the apparatus is sprung open to the open position as seen in FIG. 20, one may pull apparatus 10 off of clamps 12 with the use of ring member 120 quite easily to facilitate removal of the apparatus.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A composite umbilical cord cutter and clamp apparatus, comprising:
   a. a base member having upper and lower portions, the upper and lower portions being hinged at a first end and including lock means at a second end, so that the second ends are normally spaced apart and movable between a first, open position and a second, closed, locked position, in relation to one another;

b. housing means contained on the upper and lower portions of the base member for housing at least a pair of umbilical clamps in spaced relation, said clamps being of the type hingedly movable between open and closed positions as the base member moves between open and closed positions and said clamps being lockable in the closed position;

c. cutting means, including a blade, slidably positioned on the base member and intermediate the means for housing clamps, said cutting means being movable between the first and second ends of the base member and cutting through the umbilical cord when said base member has been locked into the closed position;

d. release means on the cutting means for unlocking the base member following the cutting movement of the blade through the umbilical cord, whereby in use the base member returns to the open position while the umbilical clamps remain in the locked position on the umbilical cord.

2. The apparatus in claim 1, wherein the release means includes a tab positioned on the cutting means to disengage a lock on the base member, so that the base member returns to the open position following the cutting movement of the blade through the umbilical cord 3. The apparatus in claim 1, further comprising holding means for removably attaching the base member to one's hand.

4. The apparatus in claim 1, wherein there is further included means for maintaining the umbilical clamps in the housing means when the base member is in the first position.

5. The apparatus in claim 1, wherein there is further included means for maintaining the blade on the second end of the base member following the cutting movement of the blade through the umbilical cord.

6. A composite umbilical cord cutter and clamp apparatus, comprising:

a. a base member having an upper portion, a lower portion, and a lock, the upper and lower portions being movably joined at a first end, a second end of the upper and lower portions being movable between a first, open position and a second, closed, locked position;

b. means contained on the upper and lower portions of the base member for housing a pair of umbilical clamp members in spaced relation, the clamp members being of the type normally biased in the open position and movable to a closed, locked position around the umbilical cord when the upper and lower portions of the base member move to the closed, locked position;

c. a slidably movable cutting blade secured in one portion of the base member to cut through the umbilical cord as the blade is moved between the first and second ends of the base member when the upper and lower portions of the base member are in the closed, locked position; and d. release means on the blade for disengaging the lock of the base member, without moving the clamps from the closed, locked position, to allow the upper and lower portions of the base member to move to the first, open position after the blade cuts through the umbilical cord.

7. The apparatus in claim 6, further comprising a pair of locked tab members on the base member which are movable to an open position after coming into contact with the release means.

8. The apparatus in claim 6, further comprising a ring member attached to the lower portion of the base member for receiving a person's index finger for assisting in pulling the base member away from the umbilical cord following cutting of the umbilical cord.

9. A hand-held composite umbilical cord cutter and clamp apparatus, comprising:

a. a base portion having upper and lower portions, the upper and lower portions being hingedly joined at a first end and having locking means at a second end, the second end being movable between a first, open position and a second, closed, locked position;

b. channel means on the upper and lower portions of the base portion for supporting a pair of umbilical clamps, the clamps being of the type normally biased in an open position, but movable to a closed, clamped position around an umbilical cord for clamping off any low of fluids through the umbilical cord;

c. a cutting blade mounted in a housing and positioned within the upper portion of the base portion, the cutting blade being slidably movable along a track within the base portion between the first and second ends thereof to cut through the umbilical cord while the base portion and umbilical clamps are in the closed, locked position; and d. a pair of tab members, positioned on the housing of the cutting blade, for contacting and disengaging the locking means of the base portion to allow and upper and lower portions of the base portion to move to the open position while the umbilical clamps remain in the closed, clamped position.

* * * * *